US005505734A

United States Patent [19]
Caniggia et al.

[11] Patent Number: 5,505,734
[45] Date of Patent: Apr. 9, 1996

[54] LOCKABLE INTRAMEDULLARY NAIL FOR THE HUMERUS

[75] Inventors: Mario Caniggia, Poggibonsi; Pietro Maniscalco, Parma, both of Italy

[73] Assignee: Gruppo Industriale Bioimpianti S.r.L., Milan, Italy

[21] Appl. No.: 318,158

[22] Filed: Oct. 5, 1994

[30] Foreign Application Priority Data

Oct. 6, 1993 [IT] Italy .................. MI93A02122

[51] Int. Cl.⁶ .................................. A61B 17/72
[52] U.S. Cl. .......................... 606/63; 606/64
[58] Field of Search .................. 606/63, 64, 62, 606/67, 68, 65, 66, 60, 72, 75, 99, 105

[56] References Cited

U.S. PATENT DOCUMENTS 2,672,861  3/1954  Jonas et al. ............... 606/63 X
3,441,017  4/1969  Kaessmann .............. 606/64 X
3,986,504  10/1976  Avila ....................... 606/63 X
5,112,333  5/1992  Fixel ......................... 606/62
5,263,955  11/1993  Baumgart et al. ........ 606/63

FOREIGN PATENT DOCUMENTS 762873  9/1980  U.S.S.R. ................... 606/63

*Primary Examiner*—Guy Tucker
*Attorney, Agent, or Firm*—Cushman Darby & Cushman

[57] ABSTRACT

A lockable intramedullary nail, suitable for treating fractures of the humerus, including a pin provided in the proximal region with a slot and with an abutment for a spring to be mounted about the pin. On the spring there acts a suitable structure for adjusting compression of the spring, including a sleeve provided with a through hole for the proximal locking of the nail, the hole being able to translate along the pin in a position facing the slot.

8 Claims, 2 Drawing Sheets 5,505,734

LOCKABLE INTRAMEDULLARY NAIL FOR THE HUMERUS

BACKGROUND OF THE INVENTION

In orthopedics, locked intramedullary nailing is normally used for treating long bone fractures.

During recent times non-locked intramedullary nails, such as Kuntscher, Rush and Ender nails, have been superseded by locked nails of the so-called "second generation" (Russel and Taylor, Gross and Kempf, etc.).

These have found wide use particularly in diaphyseal leg and femur fractures.

The difficult access paths have however been instrumental in inducing surgeons to renounce this osteosynthesis method for the upper limb in favour of external fixing and plates under compression.

The external fixing of an osteosynthesis device constitutes an obvious drawback for the patient under treatment, especially because of the continual risk of impingement.

SUMMARY OF THE INVENTION

The main object of the present invention is to provide a nail of the locked intramedullary type which allows upper limb fractures to be treated while avoiding the problem of fixation and external adjustment when fixed to the patient.

The nail of the present invention is particularly suitable for treating fractures of the humerus, which is particularly difficult for the aforesaid reasons.

This and further objects which will be apparent from the ensuing description are attained according to the present invention by a locked intramedullary nail, suitable in particular for treating fractures of the humerus, characterised by comprising a pin provided in the proximal region with a slot and with an abutment for a spring to be mounted about the pin, on the spring there acting a suitable means for adjusting its compression comprising a sleeve provided with a through hole for the proximal locking of the nail, the hole being able to translate along the pin in a position facing the slot.

BRIEF DESCRIPTION OF THE DRAWINGS

The characteristics and advantages of the invention will be more apparent from the description of one embodiment thereof given hereinafter by way of non-limiting example with reference to the figures of the accompanying drawings, in which.

DETAILED DESCRIPTION

Figure 1:
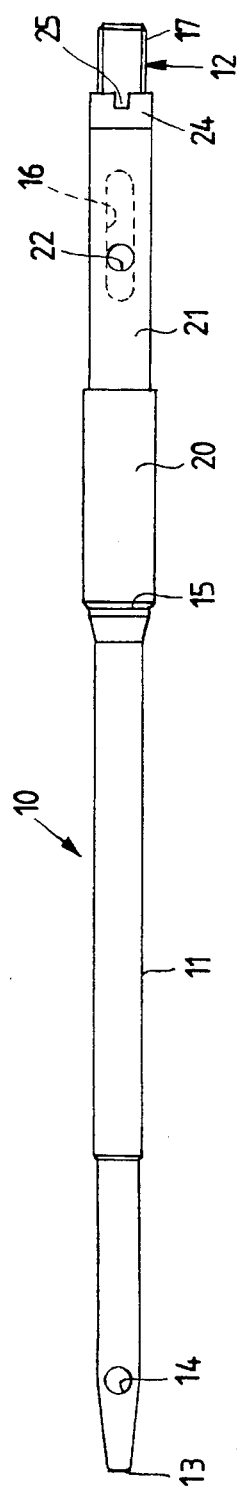
FIG. 1 is a front elevation of a nail according to the invention.
Figure 3:
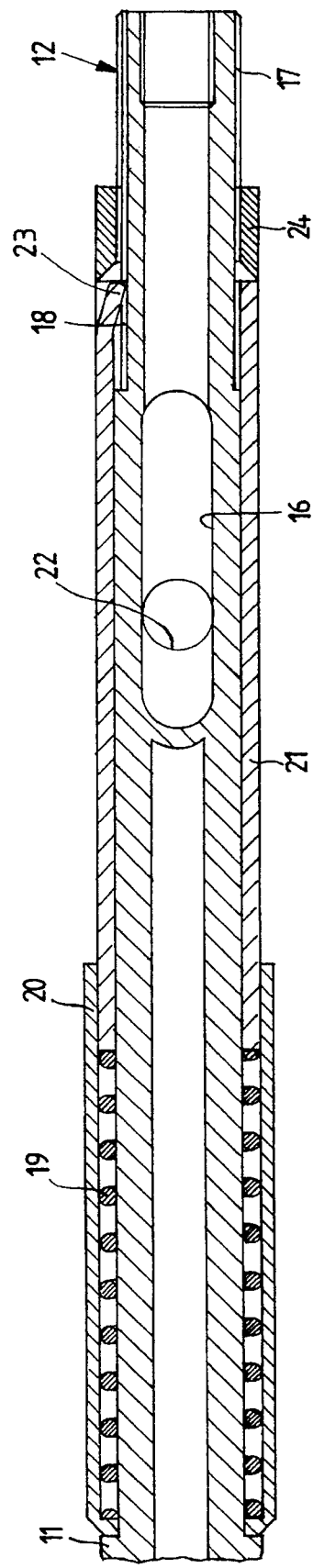
FIG. 3 is a partial longitudinal cross-section through the nail of FIG. 1.
Figure 2:
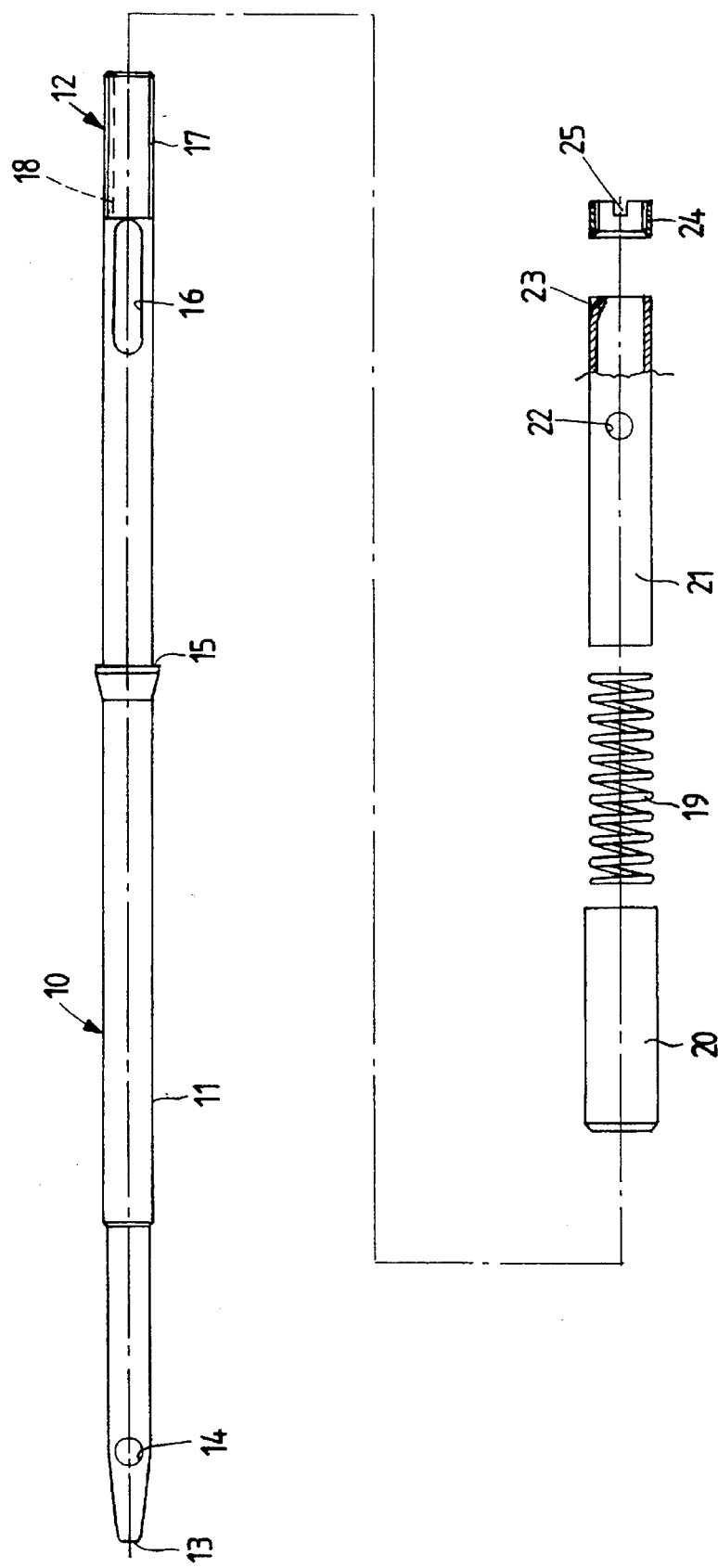
FIG. 2 is an exploded view analogous to FIG. 1.

With reference to the drawing figures, a nail 10 of the invention comprises a pin 11 consisting of a tubular element open at its proximal end 12 (with reference to its position in the bone once implanted) and closed at its distal end 13, which is also tapered. Proceeding from the distal to the proximal end, the pin 11 comprises a through hole 14, a frusto-conical taper forming an abutment 15 for the spring, a through slot 16 and an external thread 17, along a generating line of which there is a longitudinal groove 18 acting as a guide.

A spring 19 is mounted about the pin 11 from the proximal end 12, and is blocked by the abutment 15.

A sleeve 20 is provided for protecting the spring 19, plus a further sleeve 21, of lesser diameter than the spring cover sleeve 20 and having substantially the same diameter as the spring 19, so as to act as a plunger for its compression.

The sleeve 21 is provided with a through hole 22 and, at its distal end, an inwardly curved tooth 23. The tooth 23 is positioned relative to the hole 22 in the identical relationship with which the guide 18 on the pin 11 is positioned relative to the slot 16. In this manner the sleeve 21 can be mounted on the pin 11 only in the position in which the tooth 23 engages the guide groove 18, in which position the hole 22 and slot 16 face each other.

As stated, the sleeve 21 acts as a compression element for the spring 19 by interfering with its proximal end. The sleeve 21 is moved along the pin 11 by a ring 24 substantially of the same diameter, threaded internally so as to be able to be screwed on the external thread 17 of the proximal end 12 of the pin 11. The ring 24 is provided at its proximal end with a pair of facing grooves 25, to receive the head of a suitable screwdriver.

When screwed in this manner about the proximal end of the pin, it causes the sleeve 21 to slide along the pin, so compressing the proximal end of the spring 19. As the distal end of the spring 19 is blocked by the abutment 15 on the pin, this screwing of the ring 24 causes a gradual compression of the spring 19 on the pin of the nail.

Because the sleeve 21 carries the through hole 22, the sleeve 21 can be positioned at any desired point along the entire length of the slot 16 in the pin. Because the holes 14 and 22 are those used for locking the nail to the bone, it will be apparent that the nail of the invention enables the nail to be locked into the bone with a predetermined degree of compression or relaxation, depending on the particular fracture to be treated.

This will be apparent from a consideration of the following description of operation.

It will be considered for example that a nail such as the aforedescribed is to be implanted for treating a humerus fracture.

The length and diameter of the nail are determined prior to the necessary surgical operation.

This measurement can be made using the radiographic image of the integral contralateral humerus obtained with the arm abducted at 90° with the radiation source at a distance of 183 cm, or with the arm abducted and intrarotated with the radiation source at a distance of 101 cm.

The radiographic image obtained is compared with the appropriate tracing provided with the instrument set.

The surgical operation is carried out with the patient in the supine position and the shoulder to be operated slightly raised by a suitable support. It is important to use a radiotransparent operating table. If however this is not available the arm and shoulder have to be positioned external to the table (it can be useful to apply a small radiotransparent support below the scapula so as to raise the shoulder and maintain the limb to be operated external to the operating surface).

The surgeon faces the shoulder to be operated, while his or her assistant supports the arm at the elbow end.

When in this position an incision of about 4 cm is made in the anterolateral face of the shoulder (the point to locate is the anterolateral edge of the acromion); the incision is made between the front and lateral fibres of the deltoid muscle.

After incising the deltoid fibres, the rotator cuff is opened. A small longitudinal incision of about 2 cm is sufficient.

The point of entry of the nail lies between the large tuberosity and the articular surface of the head of the humerus, about 1 cm to the rear of the tendon of the long head of the bicipital muscle.

It is essential to check the exact point of entry by means of a brightness amplifier.

The nail is applied by the following steps in succession:

A) preparing the entry hole using a Kuntscher perforator;

B) reducing the fracture and introducing the guide wire with olive (80 cm length);

C) boring the intramedullary canal;

D) applying the polyethylene cannula;

E) replacing the guide wire with olive by a shorter one (50 cm) without olive;

F) applying the nail;

G) proximal locking of the synthesis means (by the hole 22);

H) distal locking of the synthesis means (by the hole 14);

I) adjusting the compression of the implanted nail.

Specifically, in implementing the foregoing steps, the Kuntscher perforator is used to prepare the entry hole; the fracture is then reduced on the guide of the brightness amplifier after which the guide wire with capsule is applied. On this the first 10 cm of the intramedullary canal are cut (the instrument set provides for 6 straight cuts of 6, 7, 9, 10 and 11 mm; in some cases, if the intramedullary canal is narrow or the spiral fracture long, it is advisable to bore the entire intramedullary canal).

The appropriate polyethylene cannula is then applied and the guide wire with olive replaced by one without olive.

After mounting the nail on the appropriate instrument, it is applied and then locked by two 4 mm cortical screws.

With the aid of the appropriate carbon instrument, this operation can be easily implemented with minimum exposure to ionizing radiation.

A cylindrical reducer is inserted into the appropriate holes to receive the tip of the drill with which the two humeral corticals are to be drilled.

The screws are then measured and applied.

After applying the intramedullary nail it is advisable to carry out radiography in the two antero-posterior and lateral projections.

At this point, three possibilities arise:

good contact between the fracture ends;

fracture diastasis;

offsetting of the fracture rima.

In the first case layer suture is used on the surgical wound, being careful to apply a stitch with non-absorbable thread on the rotator cuff. This is useful for again finding the point of application of the nail if it is to be removed.

In the second case, the nail of the invention must be compressed. This is done by a suitable screwdriver. For this purpose, the compression-relaxation ring 24 is screwed in. Two or three clockwise turns should be made at a time, and the fracture rima checked with the aid of the brightness amplifier.

If the radiographic examination shows offsetting of the fracture rima, it must be diastased. This is done by turning the compression-relaxation ring 24 anticlockwise (in this case it is advantageous to do this under radioscopy).

After the surgical operation an elastic bandage of tubigrip type is applied.

The patient immediately commences active and passive exercise of the wrist and hand.

On the third day the surgical wound is medicated and the tubigrip replaced with a brace.

The patient commences passive exercise of the elbow and continues active exercise of the wrist and hand.

During the third week passive kinesis of the shoulder is prescribed (adduction and abduction exercises).

On the 30th day a radiographic check is made, and if the formation of osseous callus is noted the brace can be removed and the limb left free. At this point the patient commences active kinesis of the shoulder.

The complete set of instruments for applying the nail of the invention is supplied in two trays, one carrying instruments and the other carrying nails and screws.

The most important instrument of the set is the insertion device, which also serves as a hole centering device for the proximal and distal locking.

An important characteristic is the material with which this instrument is constructed, namely carbon. This ensures lightness and radiotransparency.

The same insertion and centering instrument is used for all nail diameters.

A suitable trocar is used for the proximal and distal locking, the holes being made with a special drill bit with its tip pointed and with a graduated scale for facilitating the choice of screw length.

Having locked the nail with the appropriate screwdriver, the fracture can be compressed or relaxed as stated. This constitutes a basic characteristic of the nail of the invention.

The locked intramedullary nail of the invention is particularly suitable for use in treating the following fractures of the humeral diaphysis:

simple spiral fracture;

oblique simple fracture;

transverse simple fracture;

total torsion cone fracture;

total bent cone fracture;

fragmented cone fracture;

spiral comminuted complex fracture;

bifocal complex fracture;

non-spiral comminuted complex fracture.

Osteosynthesis of fractures situated 1 cm below the surgical neck of the humerus and 3 cm above the olecranon fossa can be carried out.

From the aforegoing it is apparent that the nail of the invention enables the initially stated objects to be effectively attained.

We claim:

1. A lockable intramedullary nail, suitable for treating fractures of the humerus, comprising:

a pin provided in a proximal region with a slot and provided with an abutment for a spring mounted about said pin;

on said spring there acting a suitable means for adjusting compression of said spring comprising a sleeve provided with a through hole for proximal locking of said nail, said hole being able to translate along said pin in a position facing said slot.

2. A nail as claimed in claim 1, wherein:

said pin consists of a tubular element open at an end of said proximal region and closed at and tapered leading to an end of a distal region thereof.

3. A nail as claimed in claim 1, wherein:

proceeding from a distal end to a proximal end, said pin comprises a through hole for distal locking of said nail, a frusto-conical taper acting as said abutment for said spring, said slot and an external thread, along a generating line of which there is provided a longitudinal groove acting as a guide.

4. A nail as claimed in claim 1, further comprising:

a spring cover covering said spring.

5. A nail as claimed in claim 4, wherein:

said spring is a coil spring having a circular transverse cross-sectional shape; and said sleeve has a diameter less than that of said spring cover and said sleeve has substantially the same diameter as said spring.

6. A nail as claimed in claim 3, wherein:

said sleeve is provided at a proximal end thereof with an inwardly curved tooth engaging said groove.

7. A nail as claimed in claim 1, further comprising:

said pin being threaded; and a ring threaded internally so as to be able to be screwed on the proximal end of said pin, said ring hence controlling sliding of said sleeve along said pin to compress said spring.

8. A nail as claimed in claim 7, wherein:

said ring is provided with grooves for reception of a tool for screwing said ring.

* * * * *